United States Patent
Sikkenga

(10) Patent No.: US 10,259,769 B2
(45) Date of Patent: Apr. 16, 2019

(54) CONVERSION OF POLYSTYRENE TO BENZOIC ACID

(71) Applicant: David Lee Sikkenga, Wheaton, IL (US)

(72) Inventor: David Lee Sikkenga, Wheaton, IL (US)

( * ) Notice: Subject to any disclaimer, the term of this patent is extended or adjusted under 35 U.S.C. 154(b) by 0 days.

(21) Appl. No.: 15/783,358

(22) Filed: Oct. 13, 2017

(65) Prior Publication Data

US 2019/0016659 A1 Jan. 17, 2019

Related U.S. Application Data

(60) Provisional application No. 62/532,340, filed on Jul. 13, 2017.

(51) Int. Cl.
| | | |
|---|---|---|
| C07C 51/265 | (2006.01) | |
| C07C 51/44 | (2006.01) | |
| B01J 23/889 | (2006.01) | |
| C08J 11/16 | (2006.01) | |

(52) U.S. Cl.
CPC ......... *C07C 51/265* (2013.01); *B01J 23/8892* (2013.01); *C07C 51/44* (2013.01); *C08J 11/16* (2013.01); *C08J 2325/06* (2013.01)

(58) Field of Classification Search
None
See application file for complete search history.

(56) References Cited

U.S. PATENT DOCUMENTS

2004/0019156 A1* 1/2004 Partenheimer ........... C08J 11/16
525/333.8

* cited by examiner

*Primary Examiner* — Ana Z Muresan
(74) *Attorney, Agent, or Firm* — Olson & Cepuritis, Ltd.

(57) ABSTRACT

Polystyrene-containing polymers are converted to benzoic acid by catalytic oxidation of dissolved polystyrene under elevated temperature and pressure. The produced benzoic acid is recovered by evaporation.

18 Claims, 2 Drawing Sheets

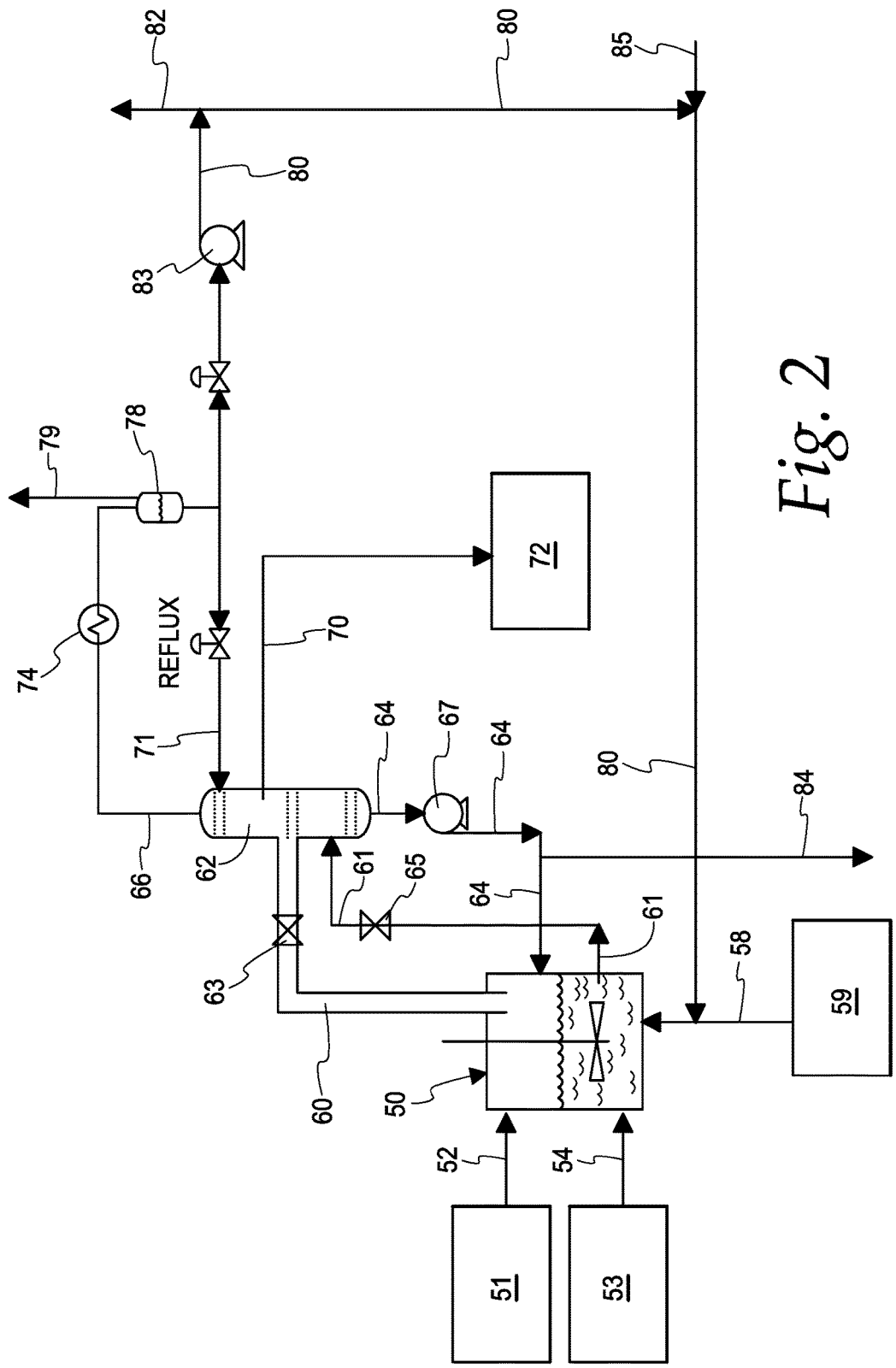

CONVERSION OF POLYSTYRENE TO BENZOIC ACID

CROSS-REFERENCE TO RELATED APPLICATIONS

This application claims the benefit of U.S. Provisional Application No. 62/532,340 filed on Jul. 13, 2017, the entire disclosure of which is incorporated herein by reference.

FIELD OF INVENTION

This invention relates to a process for oxidizing a polystyrene-containing polymer to benzoic acid.

BACKGROUND OF INVENTION

Polystyrene is a high volume polymer with many uses as a foamed product, as an injected product, and as a copolymer with other materials. Recycle and reuse of polystyrene is limited, however, due to costs of collection, purification, reformation, and reuse versus use of the virgin material. In addition, the slow biodegradation behavior of polystyrene-containing polymers results in high waste disposal costs.

Oxidation of polystyrene to benzoic acid using acetic acid is described in U.S. Pat. No. 6,958,373 to Partenheimer.

It has now been found that waste polystyrene can be efficiently converted to benzoic acid, a commercially useful compound by oxidation at elevated temperature and pressure.

SUMMARY OF INVENTION

A polystyrene-containing polymer is converted into benzoic acid by selective liquid phase oxidation of the polystyrene with water and carbon dioxide as byproducts. The produced benzoic acid is removed by evaporation and reaction product separation is achieved utilizing heat of the reaction. The physical properties of benzoic acid permit use of polystyrene-containing feedstocks containing impurities such as other polymers because the resulting oxidation products other than benzoic acid differ considerably from benzoic acid in volatility and other physical properties, thereby facilitating separation.

The conversion process comprises the steps of providing as a feedstock to an oxidizing reactor a polystyrene-containing polymer, introducing into the reactor an oxidant together with an oxidation catalyst so as to produce a reactant admixture, agitating the reactant admixture at a reactor temperature in the range of about 125° C. to about 300° C., preferably about 180° C. to about 230° C., and a reactor pressure in the range of about 1 to about 30 atmospheres for a time sufficient to convert polystyrene to benzoic acid, recovering from the reactor benzoic acid and water by evaporation, condensing the recovered benzoic acid and water, and recycling to the reactor a portion of the recovered benzoic acid and a portion of the recovered water to maintain a substantially constant benzoic acid-water mol ratio in the reactant admixture.

The oxidant is an oxygen-containing gas, preferably air.
The catalyst preferably is a heavy metal catalyst. The catalyst can be soluble or insoluble in the reactant admixture.

The present polystyrene conversion process is useful for transforming polystyrene waste into benzoic acid, a compound useful as a food preservative, for treatment of fungal skin diseases, as a precursor to plasticizers, insect repellents, artificial flavors.

BRIEF DESCRIPTION OF DRAWINGS

In the drawings,
FIG. 2 is a schematic process flow diagram of another preferred embodiment of the present invention.

DESCRIPTION OF PREFERRED EMBODIMENTS

Figure 1:
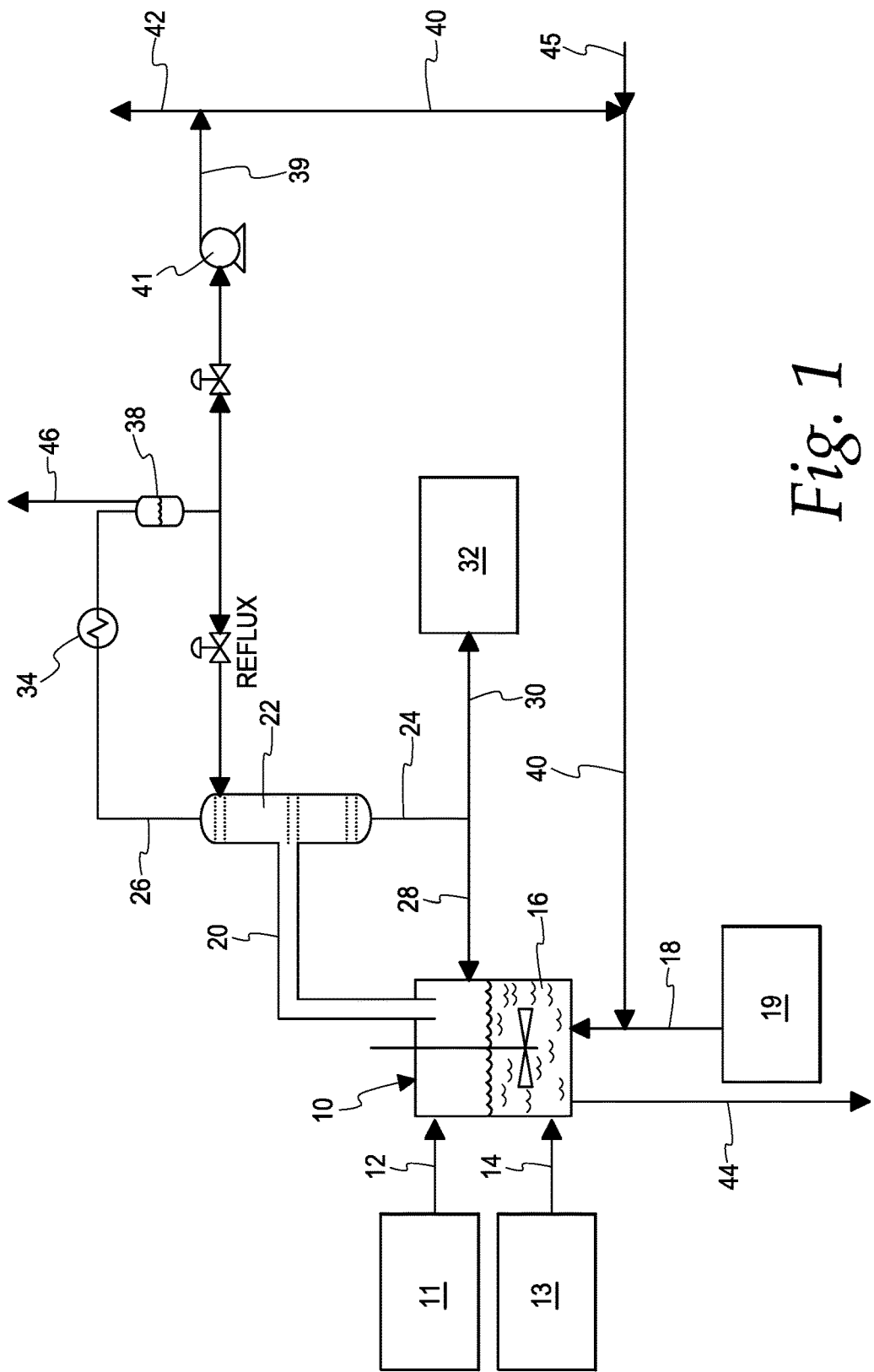
FIG. 1 is a schematic process flow diagram of a preferred embodiment of the present invention.

The present conversion process can be carried out as a batch, semi-continuous, or continuous process. The oxidation reactor can be a continuously stirred tank reactor (CSTR), or a plug flow reactor. A CSTR is preferred.

The feedstock for the present polystyrene conversion process can utilize waste polystyrene-containing polymers which include polystyrene as well as polystyrene-polybutadiene copolymers, polystyrene-poly(acrylic acid) block copolymers, polystyrene-poly(ethylene glycol) block copolymers, 2-poly(vinyl)pyridine copolymerized with styrene, and the like. The term "polystyrene" as used herein and in the appended claims means a polymer having at least two styrene units, preferably three to about 1,000 styrene units in the molecule.

Solvent for the polystyrene-containing polymers is optional and can be benzoic acid or an aromatic solvent such as toluene, and the like. The amount of solvent present in the feedstock usually is the minimum amount necessary to totally dissolve the polystyrene at the process temperature. The weight ratio of polystyrene-to-solvent in the feedstock preferably is in the range of about 2 to about 0.2.

A relatively small amount of water in the reactant admixture is desirable. Water can be introduced in the reactant admixture as part of the feedstock, which upon introduction into the reactor, will flash into vapor phase and will strip (steam distill) some of the produced benzoic acid from the liquid to the vapor. The amount of water recycled to the reactor is a variable that can be utilized to remove benzoic acid from the reactor in this manner. The amount of water fed to the reactor can be up to 5 times the weight of the polystyrene fed. The water content in the reactant admixture at reaction conditions can be up to about 6 percent by weight of the reactant admixture, preferably about 0.1 to about 3 weight percent.

A suitable oxidation catalyst is a heavy metal catalyst, preferably one soluble in the liquid reactant admixture. Typically, the oxidation catalyst includes at least one heavy metal component, i.e., a metal having atomic weight in the range of about 23 to about 200. Such metals include cobalt, manganese, vanadium, molybdenum, chromium, iron, nickel, zirconium, cerium, hafnium, platinum and the like. A particularly preferred homogeneous oxidation catalyst is a cobalt-manganese-bromide catalyst which contains ionic cobalt, manganese, and a bromide in cobalt-to-manganese molar ratios in the range of about 0.001 to 1000 and metal-to-bromide molar ratios in the range of about 10 to 0.1.

The oxidation catalyst can be introduced directly into the oxidation reactor as a solution or slurry or by premixing with the polystyrene-containing feedstock.

Use of heterogeneous oxidation catalyst containing manganese oxide or platinum on zirconia provides a processing advantage inasmuch as such catalysts are not volatile and would remain in the oxidation reactor while the produced benzoic acid is recovered from the oxidation reactor by evaporation.

The amount of the oxidation catalyst present in the liquid reactant admixture can be in the range of about 0.01 to about 5 weight percent, based on weight of the liquid reactant admixture in the oxidation reactor.

The gaseous oxidant is an oxygen containing gas such as air or a mixture of oxygen with another inert gas such as nitrogen or argon. Introduction of the gaseous oxidant into the oxidation reactor under pressure by sparging or the like can provide the necessary agitation of the liquid reactant admixture. If more intense agitation is desired, mechanical stirring can be utilized as well in lieu of, or in addition to, sparging. The gaseous oxidant is introduced into the reactor at a rate adequate to provide at least 2 mols of oxygen per unit of styrene in the polystyrene fed to the reactor. Preferably, oxygen concentration in the head space of the oxidation reactor is maintained at no more than about 10% by volume.

Conversion of polystyrene to benzoic acid can be achieved by continuous air oxidation in the process flow diagram illustrated in FIG. 1.

As shown in FIG. 1, polystyrene-containing feedstock is fed from feedstock source 11 to continuous stirred tank reactor (CSTR) 10 via conduit 12 and oxidizing catalyst solution or slurry is fed from catalyst source 13 to CSTR 10 via conduit 14 to provide a liquid reactant admixture 16 in CSTR 10.

Gaseous oxidant such as compressed air or other oxygen-containing gas is introduced into liquid reactant mixture 16 via conduit 18 from oxidant source 19 below the liquid level of reactant admixture 16. Oxygen by itself can be used as well. The oxidation reaction that takes place in CSTR 10 is exothermic, and the released heat is utilized to drive the reaction and to vaporize benzoic acid and water present in CSTR 10. Benzoic acid vapor together with water vapor, residual oxygen and inert gases leave CSTR 10 via conduit 20 and enter flash column 22 where crude molten benzoic acid is removed, usually at or below the reactor pressure as a bottoms stream via conduit 24 and water, together with light process byproducts and residual gases are removed as a vapor stream via conduit 26 which leads to condenser 34 for process heat recovery and condensation. Water and light byproduct condensate is received in condensate tank 38 equipped with vent 46 for venting residual oxygen and insert gases, and subsequent treatment to meet environmental standards, if necessary.

A portion of crude benzoic acid in the bottoms stream is returned to CSTR 10 via conduit 28 while the rest of the bottoms stream is received in crude benzoic acid storage tank 32 for further purification, if desired. A portion of the condensed water together with any light product condensate that may be present is recycled to CSTR 10 via conduit 39, pump 41 and conduit 40, preferably together with gaseous oxidant via conduit 18. In this manner plugging at the point of gaseous oxidant entry may be avoided. Additional water, if needed, is supplied to CSTR 10 via conduit 45. The rest of the water and light condensate is removed via conduit 42.

Purge conduit 44 is provided from CSTR 10 for catalyst recovery and removal of heavy byproducts that may accumulate in the oxidation reactor.

Another embodiment of the invention is illustrated in FIG. 2. In this particular embodiment, benzoic acid is recovered from the reactor at a pressure below reactor pressure. Polystyrene-containing polymer is fed to continuous stirred tank reactor (CSTR) 50 from feedstock source 51 via conduit 52. Heavy metal catalyst dissolved or slurried in benzoic acid or another suitable solvent, including water, is fed into CSTR 50 via conduit 54. Air is fed into CSTR 50 from oxidant source 59 via conduit 58. During the resulting oxidation reaction the reactant admixture is agitated by mechanical or non-mechanical stirring while benzoic acid and water vapors leave CSTR 50 via conduit 60. A liquid effluent stream leaves CSTR via conduit 61. Conduits 60 and 61 are equipped with respective back pressure control valves 63 and 65 which maintain the desired pressure in CSTR 50 while providing a relatively lower pressure downstream, usually in the range of about 1 atm to about 5 atm. The liquid effluent leaving CSTR 50 via conduit 61 will be partially flashed as it passes through back pressure control valve 65 and into flash column 62. As a result, benzoic acid and water liquids and vapors are fed into flash column 62.

Crude benzoic acid admixed with catalyst and heavy byproducts leaves the flash column 62 as a bottoms stream via conduit 64 and pump 67 and a portion thereof is returned to CSTR 50. The rest of the bottoms stream is a purge stream removed via conduit 84. If desired, the purge stream can be subjected to a separate catalyst recovery process.

Crude benzoic acid without admixed catalyst and heavy byproducts is drawn off at an intermediate stage of flash column 62 via conduit 70 to storage tank 72.

Heat recovery and attendant condensation of water and light byproducts is achieved by condenser 74 in conduit 66. The water and light product condensed from condenser 74 is received in condensate tank 78 equipped with vent 79. Effluent from vent 79 can be subjected to off-gas treatment before release in the ambient surroundings, if necessary.

A portion of condensed water and light byproduct condensate is returned via conduit 71 to flash column 62 as reflux and a portion via conduit 80 and pump 83 to CSTR 50, preferably together with gaseous oxidant stream in conduit 58. The rest of condensed water and light byproduct condensate are purged from the system via conduit 82. If additional water is needed in CSTR 50, such additional water is supplied via conduit 85.

The foregoing description and the process flow diagrams are illustrative and are not to be taken as limiting. Still other variants of the described process are possible and will readily present themselves to those skilled in the art.

The invention claimed is:

1. A process for conversion of polystyrene to benzoic acid in a liquid phase reaction which comprises
providing a feedstock comprising a polystyrene containing polymer to an oxidizing reactor;
introducing a gaseous oxidant and an oxidation catalyst into the reactor to produce a reactant admixture;
agitating the reactant admixture in the reactor at a reactor temperature in the range of about 125° C. to about 300° C. and reactor pressure in the range of about 1 to about 30 atmospheres for a time sufficient to convert polystyrene to benzoic acid;
recovering the benzoic acid and water from the reactor by evaporation;
condensing the recovered benzoic acid and water; and
recycling a portion of the recovered benzoic acid and a portion of the recovered water to the reactor in respective amounts sufficient to maintain a constant benzoic acid-water mol ratio in the reactant admixture.

2. The process in accordance with claim 1 wherein the feedstock is a molten, polystyrene containing polymer.

3. The process in accordance with claim 1 wherein the feedstock comprises polystyrene containing polymer in a solvent.

4. The process in accordance with claim 3 wherein the solvent is benzoic acid.

5. The process in accordance with claim 3 wherein the solvent is toluene.

6. The process in accordance with claim 1 wherein the recovered benzoic acid and water are condensed at a pressure lower than the reactor pressure.

7. The process in accordance with claim 1 wherein the oxidation catalyst is soluble in the reactant admixture.

8. The process in accordance with claim 1 wherein the oxidation catalyst is insoluble in the reactant admixture.

9. The process in accordance with claim 1 wherein the oxidation catalyst is a heavy metal catalyst.

10. The process in accordance with claim 1 wherein the oxidation catalyst comprises a mixture of cobalt, manganese and bromide ions.

11. The process in accordance with claim 1 wherein the oxidant is an oxygen-containing gas.

12. The process in accordance with claim 11 wherein the oxygen-containing gas is air.

13. The process in accordance with claim 1 wherein the reactant admixture contains no more than about 6 weight percent of water, based on the total weight of reactant admixture.

14. The process in accordance with claim 1 wherein the reactant admixture contains water in an amount in the range of 0.1 to about 3 weight percent, based on the total weight of the reactant admixture.

15. The process in accordance with claim 1 wherein the oxidizing reactor is a continuous stirred tank reactor.

16. The process in accordance with claim 1 wherein the reactor temperature is in the range of about 180° C. to about 230° C. and the reactor pressure is in the range of about 1 to about 30 atmospheres.

17. The process in accordance with claim 1 wherein the reactor temperature is in the range of about 180° C. to about 230° C., and benzoic acid is recovered from the reactor at a pressure below reactor pressure.

18. The process in accordance with claim 1 wherein the amount of catalyst present in the reactant admixture is in the range of about 0.01 to about 5 weight percent, based on the weight of the reactant admixture in the oxidation reactor.

* * * * *